(12) United States Patent
Ohsawa et al.

(10) Patent No.: US 6,916,849 B2
(45) Date of Patent: Jul. 12, 2005

(54) COMPOSITIONS FOR IMPROVING LIPID CONTENT IN THE BLOOD

(75) Inventors: Tsuneki Ohsawa, Tokyo (JP); Ikuo Takagi, Matsudo (JP); Ippei Shimizu, Tokyo (JP); Tatsuhito Kondo, Tokyo (JP); Masato Nakayama, Saitama (JP); Yasuhiro Torizumi, Ryugasaki (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/428,558

(22) Filed: May 1, 2003

(65) Prior Publication Data

US 2003/0220343 A1 Nov. 27, 2003

Related U.S. Application Data

(63) Continuation-in-part of application No. 10/420,442, filed on Apr. 22, 2003, now abandoned, which is a continuation-in-part of application No. PCT/JP01/09257, filed on Oct. 22, 2001.

(30) Foreign Application Priority Data

Oct. 23, 2000 (JP) .......................... 2000-322076
Dec. 18, 2000 (JP) .......................... 2000-383052

(51) Int. Cl.$^7$ ...................... A61K 31/225; A61K 31/70; A61K 31/525; A61K 31/355
(52) U.S. Cl. .......................... 514/548; 514/32; 514/251; 514/458; 514/474
(58) Field of Search .......................... 514/32, 251, 458, 514/474, 548

(56) References Cited

U.S. PATENT DOCUMENTS 5,662,934 A    9/1997  Najarian 6,245,797 B1    6/2001  Winokur
6,544,525 B1 *  4/2003  Yegorova ............... 424/195.16

FOREIGN PATENT DOCUMENTS

| GB | 2 077 264 A | 12/1981 |
| JP | 55-76816 A | 6/1980 |
| JP | 58-69813 A A | 4/1983 |
| JP | 60/41611 A | 3/1985 |
| WO | 94/15592 A1 A | 7/1994 |
| WO | 97/38694 A1 A | 10/1997 |
| WO | 99/06035 A | 2/1999 |

OTHER PUBLICATIONS

Davignon, et al.,"Comparative Efficacy and Safety of Pravastatin, Nicotinic Acid and the Two Combined in Patients with Hypercholesterolemia", Preventive Cardiology, *The American Journal of Cardiology*, Feb. 15, 1994, pp. 339–345, vol. 73.

Database CAPLUS on STN, American Chemical Society (ACS), Columbus, OH, USA), DN. 122:305890 of Salabert–Salvador, M.T. et al., QSAR relations from molecular connectivity of various physicochemical and pharmacological properties of a group of hypolipemic drugs, Ars Pharm., 1992, 33 (1–4, vol. 2), pp. 1086 to 1090.

Sulfur Amino Acids, vol. 7, No. 1, 201–205 (1984).

Grundy "Medical Intelligence, Drug Therapy," NJM, vol. 319, No. 1, Jul. 7, 1988, pp 24–33.

* cited by examiner

Primary Examiner—Phyllis G. Spivack
(74) Attorney, Agent, or Firm—Frishauf, Holtz, Goodman & Chick

(57) ABSTRACT

The present invention relates to compositions for lowering the total amount of cholesterol in the blood and methods of using the compositions. The compositions are a mixture of pravastatin and one or more vitamins selected from riboflavins, d-α-tocopherols, ascorbic acids and inositol hexanicotinate.

45 Claims, No Drawings

COMPOSITIONS FOR IMPROVING LIPID CONTENT IN THE BLOOD

This is a Continuation-in-Part Application of U.S. Ser. No. 10/420,442, filed Apr. 22, 2003 now abandoned, which is a Continuation-in-part Application of International Application No. PCT/JP01/09257 filed Oct. 22, 2001 which is incorporated herein by reference in its entirety.

BACKGROUND OF THE INVENTION

The present invention relates to compositions for lowering the total amount of cholesterol in the blood, said compositions comprising pravastatin and one or more vitamins selected from the group consisting of riboflavins, d-α-tocopherols, ascorbic acids and inositol hexanicotinate.

Pravastatin exhibits activity in lowering the total amount of cholesterol in the blood due to HMG-CoA reductase inhibition in vivo. In addition, it is known that each of riboflavins, d-α-tocopherols, ascorbic acids and inositol hexanicotinate themselves have activity in lowering the total amount of cholesterol in the blood. Furthermore, it is also known that the total amount of cholesterol in the blood can be kept at a low level and the amount of d-α-tocopherols and ascorbic acid in the body is decreased by HMG-CoA reductase inhibitors and this can be supplemented by the combination of an HMG-CoA reductase inhibitor and a d-α-tocopherol or an ascorbic acid (Japanese Patent Application Publication (Kohyo) No. Hei 8-505853).

However it has not previously been disclosed that the total amount of cholesterol in the blood is synergistically lowered by a combination of pravastatin and a riboflavin, d-α-tocopherol, ascorbic acid or inositol hexanicotinate. Pravastatin is a safe pharmaceutical agent, but it is administered for a long period. Therefore it has been required that lowering the total amount of cholesterol in the blood could be accomplished with a lower administered amount of pravastatin.

BRIEF DESCRIPTION OF THE INVENTION

The inventors of this invention have made a great effort to study compositions for lowering the total amount of cholesterol in the blood and found that lowering the total amount of cholesterol in the blood can be accomplished by a combination of pravastatin and a certain vitamin(s), even though a lower amount of pravastatin than that usually used before is administered.

The present invention is a composition for lowering the total amount of cholesterol in the blood, said composition comprising pravastatin and one or more vitamins selected from the group consisting of riboflavins, d-α-tocopherols, ascorbic acids and inositol hexanicotinate. Preferably, said composition comprises a combination of pravastatin and one or more vitamins selected from the group consisting of riboflavin tetrabutyrate, d-α-tocopherol butyrate, ascorbic acid and inositol hexanicotinate.

DETAILED DESCRIPTION OF THE INVENTION

Pravastatin (compound name: (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptane) includes the compound of the following formula and a salt (particularly sodium salt) thereof; and is prepared according to the description of the specification of Japanese Patent Application Publication No. Sho 57-2240 and is commercially available.

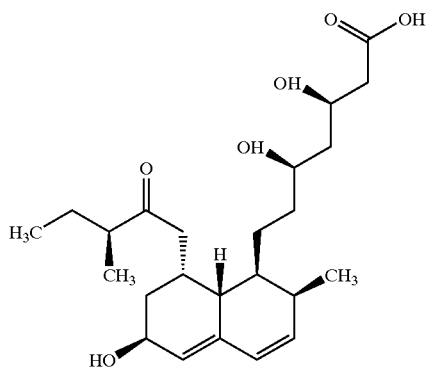

Riboflavins refer to riboflavin itself and esters of riboflavin such as riboflavin tetrabutyrate.

Tocopherols refer to tocopherol itself (racemic form and optically active form) and esters of tocopherol such as tocopherol butyrate (racemic form and optically active form).

Ascorbic acids refer to ascorbic acid itself, salts of ascorbic acid such as the sodium salt of ascorbic acid and esters of ascorbic acid such as the stearate of ascorbic acid.

Inositol hexanicotinate refers to the ester of inositol wherein six hydroxyl groups are esterified with nicotinic acid.

The total amount of cholesterol in the blood refers to the total amount of cholesterol and esters of cholesterol existing in the blood.

"Lowering" of the total amount of cholesterol in the blood means lowering to a clinically significant degree.

The solid dosage form of the composition for improving lipid content in the blood of this invention usually contains 0.01 to 5 wt % (preferably 0.05 to 3 wt %) of pravastatin; 0.002 to 40 wt % (preferably 0.01 to 20 wt %) of riboflavins; 0.05 to 50 wt % (preferably 0.5 to 25 wt %) of ascorbic acids; 0.002 to 40 wt % (preferably 0.02 to 20 wt %) of tocopherols and 0.05 to 50 wt % (preferably 0.5 to 25 wt %) of inositol hexanicotinate.

The liquid dosage form of the composition for lowering the total amount of cholesterol in the blood of this invention usually contains 0.01 to 10 mg/ml (preferably 0.05 to 5 mg/ml) of pravastatin; 0.05 to 5 mg/ml (preferably 0.1 to 3 mg/ml) of riboflavins; 1 to 10 mg/ml (preferably 3 to 7 mg/ml) of ascorbic acids; 0.5 to 5 mg/ml (preferably 1.5 to 3 mg/ml) of tocopherols; and 1 to 40 mg/ml (preferably 2 to 20 mg/ml) of inositol hexanicotinate.

An exemplary dosage form of the composition of this invention for lowering the total amount of cholesterol in the blood includes, for example, a tablet, a fine granule (including a powder), a capsule or a liquid dosage form. Each dosage form can be prepared by using an appropriate additive(s) and an active ingredient(s) according to a conventional procedure described in literature such as the Pharmacopeia of Japan.

In the dosage forms described above, various additives usually used can be employed depending on each dosage form.

For example, in the case of tablets, lactose, crystalline cellulose or the like can be used as an excipient; magnesium aluminometasilicate or the like can be used as a stabilizing agent; hydroxypropylcellulose or the like can be used as a binding agent; and magnesium stearate or the like can be used as a lubricating agent.

In the case of fine granules or capsules, lactose, purified sucrose or the like can be used as an excipient; magnesium aluminometasilicate or the like can be used as a stabilizing agent; corn starch or the like can be used an absorbing agent; and hydroxypropylcellulose, polysorbate or the like can be used as a binding agent.

In the case of liquid dosage forms, D-sorbitol solution, honey or the like can be used as a sweetening agent; dl-malic acid or the like can be used as a corrigent; disodium edatate or the like can be used a stabilizing agent; ethanol or the like can be used as a solubility-adjuvant agent; and polyoxyethylene stearate and hydrogenated castor oil 60 can be used as a solubilizing agent.

In each dosage form described hereinbefore, if necessary, a disintegrating agent such as crospovidone or the like; an absorbing agent such as calcium silicate or the like; a coloring agent such as iron sesquioxide, caramel or the like; a pH-adjusting agent such as sodium benzoate or the like and a flavoring agent can be added.

EXAMPLES

Throughout the Tables the following abbreviations are used with the following meanings.

ribo.: riboflavin, asco.: ascorbic acid, toco.: tocopherol
inos.: inositol hexanicotinate,
asco.+toco.: ascorbic acid and tocopherol
a.a.: appropriate amount, t.a.: trace amount Example 1

Tablet (1) Ingredients

TABLE 1

|  | ribo. | asco. | toco. |
|---|---|---|---|
|  | in four tablets | | |
|  | (680 mg) | (1440 mg) | (840 mg) |
| pravastatin sodium | 20 mg | 20 mg | 20 mg |
| riboflavin tetrabutyrate | 12 mg | — | — |
| ascorbic acid | — | 500 mg | — |
| tocopherol succinate | — | — | 200 mg |
| crystalline cellulose | 120 mg | 12 mg | 12 mg |
| magnesium aluminometasilicate | 144 mg | — | — |
| fatty acid ester of sucrose | — | 140 mg | 108 mg |
| Hydroxypropylcellulose | 96 mg | 48 mg | 48 mg |
| magnesium stearate | 24 mg | 24 mg | 24 mg |
| crospovidone | 100 mg | 48 mg | 48 mg |
| Lactose | a.a | a.a | a.a |

TABLE 2

|  | inos. | asco. + toco. |
|---|---|---|
|  | in four tablets | |
|  | (1400 mg) | (1400 mg) |
| pravastatin sodium | 20 mg | 20 mg |
| inositol hexanicotinate | 500 mg | — |
| Ascorbic acid | — | 500 mg |
| tocopherol succinate | — | 200 mg |
| crystalline cellulose | 12 mg | 12 mg |
| fatty acid ester of sucrose | 140 mg | 140 mg |

TABLE 2-continued

|  | inos. | asco. + taco. |
|---|---|---|
|  | in four tablets | |
|  | (1400 mg) | (1400 mg) |
| hydroxypropylcellulose | 96 mg | 48 mg |
| magnesium stearate | 24 mg | 24 mg |
| crospovidone | 100 mg | 48 mg |
| Lactose | a.a | a.a |

(2) Method for Preparation

Tablets are prepared in a similar procedure to that described in the general rules for preparation in the "tablet" section of the Pharmacopeia of Japan using the ingredients shown in Tables 1 and 2.

Example 2

Fine Granules (1) Ingredients

TABLE 3

|  | ribo. | asco. | toco. |
|---|---|---|---|
|  | in four unit dosages | | |
|  | (4 g) | (5.2 g) | (4.8 g) |
| pravastatin sodium | 20 mg | 20 mg | 20 mg |
| riboflavin tetrabutyrate | 12 mg | — | — |
| ascorbic acid | — | 1.0 g | — |
| tocopherol succinate | — | — | 200 mg |
| purified sucrose | 1.4 g | 1.6 g | 1.4 g |
| extract from stevia | — | 16 mg | — |
| corn starch | 1.2 g | 1.2 g | 1.2 g |
| polysorbate-80 | 80 mg | 48 mg | 48 mg |
| magnesium aluminometasilicate | 144 mg | — | 128 mg |
| magnesium stearate | 24 mg | 24 mg | 24 mg |
| Lactose | a.a | a.a | a.a |

TABLE 4

|  | inos. | asco. + toco. |
|---|---|---|
|  | in four unit dosages | |
|  | (5 g) | (5 g) |
| pravastatin sodium | 20 mg | 20 mg |
| inositol hexanicotinate | 1000 mg | — |
| ascorbic acid | — | 1000 mg |
| tocopherol succinate | — | 200 mg |
| purified sucrose | 1400 mg | 1600 mg |
| extract from stevia | 16 mg | 16 mg |
| corn starch | 1200 mg | 1200 mg |
| polysorbate-80 | 80 mg | 48 mg |
| magnesium aluminometasilicate | 144 mg | 144 mg |
| magnesium stearate | 24 mg | 24 mg |
| lactose | a.a | a.a |

(2) Method for Preparation

Fine granules are prepared in a similar procedure to that described in the general rules for preparation of the "granule" section of the Pharmacopeia of Japan using the ingredients shown in Tables 3 and 4.

Example 3

Capsules (1) Ingredients

TABLE 5

|  | ribo. in 4 capsules | asco. in 8 capsules | toco. in 4 capsules |
|---|---|---|---|
| pravastatin sodium | 20 mg | 20 mg | 20 mg |
| riboflavin tetrabutyrate | 12 mg | — | — |
| Ascorbic acid | — | 500 mg | — |
| tocopherol succinate | — | — | 200 mg |
| corn starch | 960 mg | 960 mg | 840 mg |
| polysorbate-80 | 80 mg | 48 mg | 48 mg |
| magnesium aluminometasilicate | 144 mg | — | 128 mg |
| magnesium stearate | 24 mg | 24 mg | 24 mg |
| Lactose | a.a | a.a | a.a |
| Subtotal | 1520 mg | 1940 mg | 1580 mg |
| Capsule | 320 mg | 640 mg | 320 mg |
| Total | 1840 mg | 2580 mg | 1900 mg |

TABLE 6

|  | inos. in 8 capsules | asco. + toco. in 8 capsules |
|---|---|---|
| pravastatin sodium | 20 mg | 20 mg |
| inositol hexanicotinate | 500 mg | — |
| Ascorbic acid | — | 500 mg |
| tocopherol succinate | — | 200 mg |
| corn starch | 960 mg | 960 mg |
| polysorbate-80 | 80 mg | 48 mg |
| magnesium aluminometasilicate | 144 mg | 144 mg |
| magnesium stearate | 24 mg | 24 mg |
| Lactose | a.a | a.a |
| Subtotal | 2000 mg | 2000 mg |
| Capsule | 640 mg | 640 mg |
| Total | 2640 mg | 2640 mg |

(2) Method for Preparation

Capsules are prepared in a similar procedure to that described in the general rules for preparation in the "granule" section of the Pharmacopeia of Japan using the ingredients shown in Tables 5 and 6, followed by filling the resulting fine granules into each capsule.

Example 4

Liquid Dosage Forms (1) Ingredients

TABLE 7

|  | ribo. | asco. in 100 ml | toco. |
|---|---|---|---|
| pravastatin sodium | 20 mg | 20 mg | 20 mg |
| riboflavin sodium phosphate | 20 mg | — | — |
| ascorbic acid | — | 500 mg | — |
| d-α-tocopherol acetate | — | — | 50 mg |
| D-sorbitol solution (70%) | 4 g | 6 g | 4 g |
| Honey | 7 g | 8 g | 7 g |
| dl-malic acid | 200 mg | — | 200 mg |
| sodium edetate | 20 mg | 20 mg | 20 mg |
| Ethanol | 2 ml | 2 ml | 2 ml |
| polyoxyethylene stearate hydrogenated castor oil 60 | 100 mg | 100 mg | 100 mg |
| sodium benzoate | 60 mg | 60 mg | 60 mg |
| flavoring agent | t.a. | t.a. | t.a. |
| purified water | a.a. | a.a. | a.a |

TABLE 8

|  | inos. | asco. + toco. in 100 ml |
|---|---|---|
| pravastatin sodium | 20 mg | 20 mg |
| inositol hexanicotinate | 500 mg | — |
| ascorbic acid | — | 500 mg |
| d-α-tocopherol acetate | — | 50 mg |
| D-sorbitol solution (70%) | 4 g | 6 g |
| honey | 7 g | 8 g |
| dl-malic acid | 200 mg | 200 mg |
| sodium edetate | 20 mg | 20 mg |
| ethanol | 2 ml | 2 ml |
| polyoxyethylene stearate hydrogenated castor oil 60 | 100 mg | 100 mg |
| sodium benzoate | 60 mg | 60 mg |
| flavoring agent | t.a. | t.a. |
| purified water | a.a. | a.a. |

(2) Method for Preparation

Liquid dosage forms are prepared in a similar procedure to that described in the general rules for preparation in the "liquid dosage form" section of the Pharmacopeia of Japan using the ingredients shown in Tables 5 and 6.

Example 5

Evaluation of Serum Lipid Level

Test Method (1) Test Substance

Pravastatin with a purity of 99.4%, manufactured at Sankyo Co. Ltd., was employed in the study. Riboflavin acetate, d-α-tocopherol acetate, ascorbic acid, and inositol hexanicotinate were purchased from Mitsubishi Tokyo Pharmaceutical Co., Eisai, Nippon Roche K.K., and Shiratori Pharmaceutical Co. Ltd., respectively.

(2) Test Animal

Male beagle dogs were purchased at 5 months old from Covance Research Products Inc., as the test animals, and were used after quarantine and acclimatization periods of approximately 1 month.

(3) Dosage Form, Preparation and Storage of the Dosage Form

The required amounts of pravastatin or each combination drug as calculated based on the body weight of each animal were placed in a gelatin capsule (½-ounce volume) purchased from TORPAC Co. Capsules filled with pravastatin were stored in a cold room and with combination drugs at room temperature until use.

Combination drugs were put in identical geltin capsules.

(4) Route of Administration and Administration Period

Capsules filled with pravastatin or combination drugs were orally administered once daily between 9:00 and 12:30 to the test animals. All test animals were fasted 2–3 hr prior to administration. The administration period was 11 successive days.

(5) Preparation of Test Samples and Assay Methods

Approximately 10 ml of blood were collected from the cephalic vein on 14 and 7 days before administration (2 and one week before the drug administration) and 4, 8, and 12 days after administration of the capsules. The animals were fasted for approximate 18 hr prior to blood collection. Collected blood was placed into test tubes and left for 0.5–1 hr at room temperature. The test tubes were then centrifuged at 3,000 rpm for 10 min to isolate serum. Levels of total cholesterol and ALP in the serum were determined by the CEH-COD-POD and Bessey-Lowry methods, respectively.

For quantitative analyses, an automatic analyzer, Monarch (Instrumentation Laboratory), was used.

Results

Levels of serum lipids following single or combined administration of pravastatin, riboflavin acetate, d-α-tocopherol acetate, ascorbic acid, and inositol hexanicotinate relative to their average serum levels 2 and one week before administration (100) were calculated. Each value represents the mean value calculated from 5 animals.

(Effects of Co-administered Pravastatin and Riboflavin Acetate)

TABLE 9

| Test substance | Total Cholesterol Level in Serum After Administration | | |
|---|---|---|---|
| (mg/kg) | 4 days | 8 days | 12 days |
| Pravastatin alone (2) | 93.6 | 90.0 | 93.0 |
| Riboflavin acetate alone (6) | 103.9 | 101.6 | 100.5 |
| Pravastatin (2) + Riboflavin acetate (6) | 91.4 | 82.6 | 85.8 |

TABLE 10

| Test substance | ALP level (after administration) | | |
|---|---|---|---|
| (mg/kg) | 4 days | 8 days | 12 days |
| Pravastatin alone (2) | 97.4 | 96.7 | 92.2 |
| Riboflavin acetate alone (6) | 98.1 | 98.8 | 93.9 |
| Pravastatin (2) + Riboflavin acetate (6) | 90.8 | 89.1 | 89.5 |

(Effects of Co-administered Pravastatin and d-α-tocopherol Acetate)

TABLE 11

| Test substance | Total Cholesterol Level in Serum After Administration | | |
|---|---|---|---|
| (mg/kg) | 4 days | 8 days | 12 days |
| Pravastatin alone (2) | 93.6 | 90.0 | 93.0 |
| d-α-tocopherol acetate alone (10) | 96.3 | 92.8 | 95.9 |
| Pravastatin (2) + d-α-tocopherol acetate (10) | 92.8 | 82.7 | 79.3 |

(Effects of Co-administered Pravastatin and Ascorbic Acid)

TABLE 12

| Test substance | Total Cholesterol Level in Serum After Administration | | |
|---|---|---|---|
| (mg/kg) | 4 days | 8 days | 12 days |
| Pravastatin alone (2) | 93.6 | 90.0 | 93.0 |
| Ascorbic acid alone (50) | 98.7 | 98.2 | 103.4 |
| Pravastatin (2) + Ascorbic acid (50) | 89.4 | 84.1 | 80.9 |

(Effects of Co-administered Pravastatin and Inositol Hexanicotinate)

TABLE 13

| Test substance | Total Cholesterol Level in Serum After Administration | | |
|---|---|---|---|
| (mg/kg) | 4 days | 8 days | 12 days |
| Pravastatin alone (2) | 93.6 | 90.0 | 93.0 |
| Inositol hexanicotinate (400) | 99.2 | 99.8 | 100.0 |
| Pravastatin (2) + Inositol hexanicotinate (400) | 86.5 | 83.3 | 81.6 |

(Effects of Co-administered Pravastatin, d-α-tocopherol Acetate, and Ascorbic Acid)

TABLE 14

| Test substance | Total Cholesterol Level in Serum After Administration | | |
|---|---|---|---|
| (mg/kg) | 4 days | 8 days | 12 days |
| Pravastatin alone (2) | 93.6 | 90.0 | 93.0 |
| d-α-tocopherol acetate alone (10) | 97.8 | 96.4 | 96.1 |
| Pravastatin (2) + d-α-Aocopherol acetate (10) + ascorbic acid (50) | 89.3 | 87.8 | 82.4 |

The composition of the present invention comprising a combination of pravastatin and ascorbic acid and/or the like exhibits excellent activity for lowering the total amount of cholesterol in the blood and is useful as an agent for lowering the total amount of cholesterol in the blood.

Although the dose of compounds used according to the invention may widely vary depending on the extent of diseases and age of patients, (e.g. a human patient), the dose of one administration of pravastatin is normally within the range of from 0.01 mg/kg to 10 mg/kg, preferably from 0.1 mg/kg to 1 mg/kg, administered once or several times a day depending on the extent of diseases.

The dose of one administration of riboflavins is normally within the range of from 0.004 mg/kg to 24 mg/kg, preferably from 0.04 mg/kg to 2.4 mg/kg, administered once or several times a day depending on the extent of diseases.

The dose of one administration of tocopherols is normally within the range of from 0.02 mg/kg to 60 mg/kg, preferably from 0.2 mg/kg to 6 mg/kg, administered once or several times a day depending on the extent of diseases.

The dose of one administration of ascorbic acids is normally within the range of from 0.1 mg/kg to 400 mg/kg, preferably from 1 mg/kg to 40 mg/kg, administered once or several times a day depending on the extent of diseases.

The dose of one administration of inositol hexanicotinate is normally within the range of from 0.16 mg/kg to 36 mg/kg, preferably from 1.6 mg/kg to 3.6 mg/kg, administered once or several times a day depending on the extent of diseases.

What is claimed is:

1. A pharmaceutical composition for lowering the total amount of cholesterol in the blood, said composition comprising pravastatin and one or more vitamins selected from the group consisting of riboflavins, d-α-tocopherols, ascorbic acids and inositol hexanicotinate in amounts to form a synergistically effective mixture.

2. A composition according to claim 1 in solid dosage form containing 0.01 to 5 wt % pravastatin and one or more vitamins in the following amounts 0.002 to 40 wt % of riboflavins; 0.05 to 50 wt % of ascorbic acids; 0.002 to 40 wt % of tocopherols and 0.05 to 50 wt % of inositol hexanicotinate.

3. A composition according to claim 2, comprising said riboflavins and wherein said riboflavins are selected from the group consisting of riboflavin and esters thereof.

4. A composition according to claim 3, wherein said riboflavins are riboflavin.

5. A composition according to claim 3, wherein said riboflavins are riboflavin sodium phosphate.

6. A composition according to claim 3, wherein said riboflavins are riboflavin tetrabutyrate.

7. A composition according to claim 2, comprising said d-a-tocopherels wherein said d-α-tocopherols are selected from the group consisting of d-α-tocopherol and esters thereof.

8. A composition according to claim 7, wherein said d-α-tocopherols are d-α-tocopherol acetate.

9. A composition according to claim 7, wherein said d-α-tocopherols are d-α-tocopherol butyrate.

10. A composition according to claim 7, wherein said d-α-tocopherols are d-α-tocopherol succinate.

11. A composition according to claim 2, comprising said ascorbic acids and wherein said ascorbic acids are selected from the group consisting of ascorbic acid, esters of ascorbic acid and salts of ascorbic acid.

12. A composition according to claim 11, wherein said ascorbic acids are ascorbic acid.

13. A composition according to claim 11, wherein said ascorbic acids are stearate of ascorbic acid.

14. A composition according to claim 2, wherein said vitamins are selected from the group consisting of riboflavins, d-α-tocopherols and ascorbic acids.

15. A composition according to claim 1 in liquid dosage form containing 0.01 to 10 mg/ml pravastatin and one or more vitamins in the following 0.05 to 5 mg/ml of riboflavins; 1 to 10 mg/ml of ascorbic acids; 0.05 to 5 mg/ml of tocopherols and 1 to 40 mg/ml of inositol hexanicotinate.

16. A composition according to claim 2, further comprising a pharmaceutically acceptable additive selected from the group consisting of an excipient, stabilizing agent, binding agent, lubricating agent, disintegrating agent, absorbing agent, coloring agent, pH adjusting agent and flavoring agent.

17. A composition according to claim 15, comprising said riboflavins and wherein said riboflavins are selected from the group consisting of riboflavin and esters thereof.

18. A composition according to claim 17, wherein said riboflavins are riboflavin.

19. A composition according to claim 17, wherein said riboflavins are riboflavin sodium phosphate.

20. A composition according to claim 17, wherein said riboflavins are riboflavin tetrabutyrate.

21. A composition according to claim 15, comprising said d-α-tocopherols wherein said d-α-tocopherols are selected from the group consisting of d-α-tocopherol and esters thereof.

22. A composition according to claim 21, wherein said d-α-tocopherols are d-α-tocopherol acetate.

23. A composition according to claim 21, wherein said d-α-tocopherols are d-α-tocopherol butyrate.

24. A composition according to claim 21, wherein said d-α-tocopherols are d-α-tocopherol succinate.

25. A composition according to claim 15, comprising said ascorbic acids and wherein said ascorbic acids are selected from the group consisting of ascorbic acid, esters of ascorbic acid and salts of ascorbic acid.

26. A composition according to claim 25, wherein said ascorbic acids are ascorbic acid.

27. A composition according to claim 25, wherein said ascorbic acids are otearate of ascorbic acid.

28. A composition accoiding to claim 15, wherein said vitamins are selected from the group consisting of riboflavins, d-α-tocopherols and ascorbic acids.

29. A composition according to claim 15, further comprises a pharmaceutically acceptable additive selected from the group consisting of a sweetening agent, a corrigent, stabilizing agent, solubility adjuvant agent, solubilizing agent, coloring agent, pH adjusting agent and a flavoring agent.

30. A method for lowering the total amount of cholesterol in the blood of a mammal comprising administering to said mammal synergistically effective amounts of pravastatin and of one or more vitamins selected from the group consisting of riboflavins, d-α-tocopherols, ascorbic acids and inositol hexanicotinate to form a synergistically effective mixture.

31. A method according to claim 30, wherein said riboflavins are administered and are selected from the group consisting of riboflavin and esters thereof.

32. A method accordin to claim 31, wherein said riboflavins are aelected from the group consisting of riboflavin, riboflavin sodium phosphate, and riboflavin tetrabutyrate.

33. A method according to claim 30, wherein said d-α-tocopherols are administered and are selected from the group consisting of d-α-tocopherol and esters thereof.

34. A method according to claim 33, wherein said d-α-tocopherols are selected from the group consisting of d-α-tocopherol acetate, d-α-tocopherol butyrate and d-α-tocopherol succinate.

35. A method according to claim 30, wherein said ascorbic acids are administered and are selected from the group consisting of esters of ascorbic acid and salts of ascorbic acid.

36. A method acoording to claim 30, wherein said ascorbic acids are administered and are selected from the group consisting of ascorbic acid and the stearate of ascorbic acid.

37. A method according to claim 30, wherein said vitamins are selected from the group consisting of riboflavins, d-α-tocopherols and ascorbic acid.

38. A method according to claim 30, comprising administering pravastatin and riboflavin tetrabutyrate.

39. A method according to claim 30, comprising administering pravaseatin and riboflavin sodium phosphate.

40. A method according to claim 30, comprising administering pravastatin and d-α-tocopherol butyrate.

41. A method according to claim 30, comprising administering pravastatin and d-α-tocopherol succinate.

42. A method according to claim 30, comprising administering pravastatin and d-α-tocopherol sodium phosphate.

43. A method according to claim 30, comprising administering pravastatin and asccrbic acid.

44. A method accordinq to claim 30, comprising administering pravastatin and inositol hexanicotinate.

45. A method according to claim 30, wherein said mammal is human.

* * * * *